US008932854B2

(12) United States Patent
Kobayashi et al.

(10) Patent No.: US 8,932,854 B2
(45) Date of Patent: Jan. 13, 2015

(54) ADSORBENT FOR LYMPHOCYTE PROLIFERATION INHIBITOR AND TREATING METHOD

(75) Inventors: Akira Kobayashi, Hyogo (JP); Shinya Yoshida, Hyogo (JP); Katsuo Noguchi, Tokyo (JP)

(73) Assignee: Kaneka Corporation, Osaka (JP)

( * ) Notice: Subject to any disclaimer, the term of this patent is extended or adjusted under 35 U.S.C. 154(b) by 742 days.

(21) Appl. No.: 12/771,373

(22) Filed: Apr. 30, 2010

(65) Prior Publication Data

US 2010/0221832 A1 Sep. 2, 2010

Related U.S. Application Data

(62) Division of application No. 11/575,024, filed as application No. PCT/JP2005/016601 on Sep. 9, 2005, now abandoned.

(30) Foreign Application Priority Data

Sep. 10, 2004 (JP) .................................. 2004-264044

(51) Int. Cl.
| C12N 5/078 | (2010.01) |
| C12N 5/02 | (2006.01) |
| A61K 35/14 | (2006.01) |
| A61M 1/36 | (2006.01) |
| C12N 5/0783 | (2010.01) |

(52) U.S. Cl.
CPC .............. *A61K 35/17* (2013.01); *A61M 1/3679* (2013.01); *C12N 5/0636* (2013.01); *C12N 2533/00* (2013.01); *C12N 2533/30* (2013.01)
USPC ...... 435/372; 435/325; 435/372.2; 435/372.3

(58) Field of Classification Search
CPC ..... A61K 35/16; A61K 35/17; C12N 5/0636; C12N 33/30
USPC ............................ 435/325, 372, 372.2, 372.3
See application file for complete search history.

(56) References Cited

U.S. PATENT DOCUMENTS

| 4,140,652 | A | | 2/1979 | Korshak et al. |
| 5,725,768 | A | | 3/1998 | Adachi et al. |
| 5,773,384 | A | * | 6/1998 | Davankov et al. ............ 502/402 |
| 6,497,675 | B1 | * | 12/2002 | Davankov ..................... 604/6.09 |
| 2001/0031701 | A1 | | 10/2001 | Shimbo et al. |
| 2002/0115585 | A1 | * | 8/2002 | Hei ................................... 514/1 |

FOREIGN PATENT DOCUMENTS

| EP | 0319961 | 6/1989 |
| EP | 0483765 | 5/1992 |
| EP | 0483765 A2 | 5/1992 |
| EP | 1132737 | 9/2001 |
| JP | 56092824 | 7/1981 |
| JP | 61-277628 | 12/1986 |
| JP | 63-283748 | 11/1988 |
| JP | 2-193069 | 7/1990 |
| JP | 4-170965 | 6/1992 |
| JP | 6312135 | 11/1994 |
| JP | 8257398 | 10/1996 |
| JP | 10290689 | 11/1998 |
| JP | 2000245451 | 9/2000 |
| JP | 2001218840 | 8/2001 |
| JP | 2001324487 | 11/2001 |
| JP | 2002539178 | 11/2002 |
| JP | 2002360690 | 12/2002 |
| JP | 2003083946 | 3/2003 |
| JP | 2003310751 | 11/2003 |
| JP | 2003339854 | 12/2003 |
| JP | 2004073618 | 3/2004 |
| JP | 2004249094 | 9/2004 |
| WO | WO-0055621 | 9/2000 |
| WO | WO-03057356 | 7/2003 |

OTHER PUBLICATIONS

Resins and Media. Supelco. downloaded on Sep. 4, 2012 from http://www.supelco.com.tw/B-11%20%20429-456.pdf. p. 429-456.*
Han et al. Simplified Whole Blood Method for Evaluating in Vitro Lymphocyte Reactivity of Laboratory Animals. Clin. exp. Immunol. (1972) 11, 137-142.*
Skea et al. Large Ex Vivo Expansion of Human Umbilical Cord Blood CD41 and CD81 T Cells. Journal of Hematotherapy 8:129-139 (1999).*
Bio-Rad. Bio-Beads SM-2 Adsorbents. downloaded on May 21, 2014 from http://www.bio-rad.com/en-us/product/bio-beads-sm-2-adsorbents. p. 1.*

(Continued)

*Primary Examiner* — Taeyoon Kim
(74) *Attorney, Agent, or Firm* — Novak Druce Connolly Bove + Quigg LLP

(57) ABSTRACT

The invention relates to a porous material for body fluid treatment for promoting lymphocyte proliferation in lymphocyte culture which contains a high-molecular compound having an angle of contact with water within the range of 40 to 98°, and a porous material for body fluid treatment which comprises activated carbon; and also relates to a treatment device wherein the porous material is used; a method for proliferating lymphocytes; a method for producing mammalian lymphocytes; a method for producing a pharmaceutical composition; an additive body fluid to be added to a culture medium on the occasion of lymphocyte culture; a method for treating a disease against which a therapeutic effect is produced by returning extracorporeally activated mammalian lymphocytes into the body; and a method of manufacturing the porous materials for body fluid treatment for promoting the lymphocyte proliferation in lymphocyte culture.

12 Claims, No Drawings

(56) References Cited

OTHER PUBLICATIONS

An Introduction to Biomaterials. 2006. The Biomedical Engineering Series. edited by Scott A. Guelcher, Jeffrey O. Hollinger. p. 1, 2 and 21.
Bio-Beads S-X Beads. 2009. Instruction manual (www.bio-rad.com/LifeScience/pdf/Bulletin_9142.pdf). p. 1-21.
Perkins et al. 1973. Gel Permeation Chromatography of Heated Fats. J. Arnerical Oil Chem, Soc. vol. 50:223-225.
Moy et al. 1994. Contact angle studies of the surface of covalently bonded poly-L-lysine to surfaces treated by glow-discharge. Colloid Polym Sci 272:1245-1251.
Extended European Search Report issued in related European Patent Application No. 05782324.7, Dec. 1, 2010, p. 1-7.
Database WPI Week 198901 Thomson Scientific, London, GB; AN 1989-004333 (XP002609763), abstract for JP-63-283748, Nov. 24, 2010, p. 1.

* cited by examiner

ADSORBENT FOR LYMPHOCYTE PROLIFERATION INHIBITOR AND TREATING METHOD

RELATED APPLICATIONS

This application is a divisional of co-pending application Ser. No. 11/575,024, filed on Oct. 19, 2007, which is a national phase filing under 35 U.S.C. §371 of International Application No. PCT/JP05/016601 filed on Sep. 9, 2005; and this application claims priority to Application No. 2004-264044 filed in Japan on Sep. 10, 2004 under 35 U.S.C. §119; the entire contents of all are hereby incorporated by reference.

TECHNICAL FIELD

The present invention relates to a porous material for overcoming the lymphocyte proliferation inhibition in lymphocyte culture in activated autologous lymphocyte therapy, among others, which comprises taking immunocompetent cells (lymphocytes in particular) in blood out of the body, culturing them for stimulation/activation and for proliferation and again returning them into the body to thereby preventing the advance of cancer, an infectious disease or an immune disease, and to a device for lymphocyte proliferation wherein the porous material mentioned above is utilized. Furthermore, it relates to a method for preparing a body fluid with a reduced lymphocyte proliferation inhibitor concentration as well as to a method for proliferating lymphocytes using a medium with such body fluid added thereto.

BACKGROUND ART

In recent years, attention has been focused on activated autologous lymphocyte therapy, which comprises taking immunocompetent cells (lymphocytes in particular) in blood out of the body, culturing them for stimulation/activation and for proliferation and again returning them into the body to thereby prevent the advance of cancer. This technique produces little side effects and makes it possible to maintain the quality of life (QOL) at high levels even during treatment and, therefore, is becoming more and more popular in the field of cancer treatment as a fourth choice of cancer therapy next to the three major cancer treatment methods, namely surgical therapy, radiotherapy and chemotherapy. The technique is already in actual use as one of tailor-made highly advanced medical treatment methods in university hospitals, cancer centers and specialized clinics and, expectedly, it will be used still more widely. This technique generally comprises collecting a portion of the blood of a patient, separating a lymphocyte fraction by density gradient centrifugation, adding the autologous plasma to a medium for exclusive use and cultivating the lymphocytes. Generally, the number of lymphocytes arrives at about 100 times the number of lymphocytes in the primary culture in a week. It has become known, however, that there are some such cancer patients that lymphocytes derived therefrom can hardly proliferate in the presence of autologous plasma but can proliferate in the presence of the plasma derived from another person (resulting from blood donation). Cancer cells produce cellular immunity inhibiting factors, for example such cytokines as transforming growth factor beta (hereinafter abbreviated as TGF-β), interleukin 4 (hereinafter abbreviated as IL4), interleukin 6 (hereinafter abbreviated as IL6) and interleukin 10 (hereinafter abbreviated as IL10) as well as prostaglandin E2 (hereinafter abbreviated as PGE2). Thus, the possibility is suggested that such factors might inhibit the proliferation of lymphocytes. However, the concentrations of these factors in the blood of cancer patients are almost the same as those in persons in normal health, although their local concentrations in cancer foci are high. Further, when such factors commercially available as reagents are dissolved in plasma at high concentrations and the influences thereof on lymphocyte proliferation are examined, little inhibition is observed. Such and other findings suggest that there is an unknown mechanism other than the involvement of such factors.

As a matter of fact, an adsorbent for adsorptively removing immunosuppressive acidic proteins (IAPs) (Patent Document 1), an adsorbent for adsorptively removing interleukins in body fluids (Patent Document 2) and an adsorbent capable of adsorbing TGF-β in body fluids (Patent Document 3), among others, have so far been disclosed. However, all of them are limited in scope to the adsorptive removal of cytokines and there is no report about an adsorbent capable of improving the proliferative activity of lymphocytes. In recent years, the number of patients having activated lymphocyte therapy has been increasing year by year with the marked advance of such therapy and, on the other hand, the number of patients relying on blood donation because of poor lymphocyte proliferation has also been increasing. In the case of blood donation, it is necessary to secure non-autologous plasma in conformity with patient's therapeutic cycle. Further, there are a number of problems to be taken up from the safety viewpoint, for example the risk of infection; therefore, it is desired that a method for overcoming the lymphocyte proliferation inhibition in lymphocyte culture by a simple procedure without losing other useful substances be developed. Furthermore, in cancer patients as well whose lymphocyte can proliferate in the presence of autologous body fluids, it is expected that further improvements in proliferation rate and in cytokine producing activity, for instance, be achieved when the inhibition of lymphocyte proliferation in lymphocyte culture is broken down. Currently, however, neither adsorbent, nor porous body, nor device nor treatment method is available for such purposes. Further, adsorbents prepared by causing a material capable of adsorbing cytokines and like immunosuppressive proteins to bind to a water-insoluble carrier have been disclosed (Patent Document 4 to 6). However, the effect of those adsorbents depends on an affinity between an amine residue and such immunosuppressive proteins as cytokines. Therefore, those adsorbents require the presence of an amine residue.

At present, a treatment is eagerly anticipated which will promote the proliferation of those lymphocytes which are in a poorly proliferative condition in lymphocyte culture for the treatment of a disease against which a therapy comprising returning activated lymphocytes again into the body, typically activated autologous lymphocyte therapy, is therapeutically effective.

Patent Document 1: Japanese Kokai Publication Sho-56-092824

Patent Document 2: Japanese Kokai Publication Hei-08-257398

Patent Document 3: Japanese Kokai Publication 2001-218840

Patent Document 4: Japanese Kokai Publication 2003-310751

Patent Document 5: Japanese Kokai Publication 2003-339854

Patent Document 6: Japanese Kokai Publication 2004-73618

SUMMARY OF THE INVENTION

Accordingly, it is an object of the present invention to provide an adsorbent useful in such treatment for promoting lymphocyte proliferation, a method for such treatment, and lymphocytes proliferated by treatment with the porous material.

The present inventors made intensive investigations in search of a porous material capable of breaking down the inhibition of lymphocyte proliferation while minimizing the loss of useful substances necessary for the proliferation of lymphocytes, etc. and, as a result, found that when a subject-derived body fluid is treated in advance with a water-insoluble porous material containing a high-molecular compound having an angle of contact with water within the range of about 40° to 98° or a porous material containing activated carbon, the lymphocyte proliferation rate in lymphocyte culture is markedly improved. Such and other findings have now led to completion of the present invention.

Thus, the present invention relates to a porous material for body fluid treatment for promoting lymphocyte proliferation in lymphocyte culture which contains a high-molecular compound having an angle of contact with water within the range of 40° to 98°; and to a porous material for body fluid treatment for promoting lymphocyte proliferation in lymphocyte culture which comprises activated carbon.

The invention also relates to a treatment device for promoting the lymphocyte proliferation in lymphocyte culture which comprises the above-mentioned porous material and a container therefor.

Further, the invention relates to a method for proliferating lymphocytes;

a method for producing mammalian lymphocytes;

a method for producing a pharmaceutical composition;

an additive body fluid to be added to the culture medium on the occasion of lymphocyte culture;

a method for treating a disease against which returning extracorporeally activated mammalian lymphocytes into the body is therapeutically effective; and a use of activated carbon or a high-molecular compound having an angle of contact with water within the range of 40° to 98° in producing a porous material for body fluid treatment to promote the lymphocyte proliferation in lymphocyte culture.

DETAILED DESCRIPTION OF THE INVENTION

First, the porous material of the invention is described.

The porous material of the invention is a porous material for use in body fluid treatment for promoting the lymphocyte proliferation in lymphocyte culture which contains a high-molecular compound having an angle of contact with water within the range of 40° to 98°.

In the practice of the invention, the angle of contact with water can be determined by preparing a smooth film specimen constituted of the high-molecular compound, which is the main constituent of the porous material, forming a liquid drop on the film in a horizontal state using a microinjector and measuring the contact angle at room temperature. When the porous material is soluble in an organic solvent, the contact angle can also be measured after dissolving the porous material and preparing a cast film specimen on a flat sheet using the resulting solution. For details of the measurement method, reference can be made, for example, to "Shin-Jikken Kagaku Koza (Lectures in Experimental Chemistry, New Series) 18: Kaimen to Koroido (Interface and Colloid)" (First Edition, published October 20, Showa 52 (1977) by Maruzen Co., Ltd.). Thus, a flat sheet specimen having a mirror-finish level of smoothness is placed horizontally so that the atmosphere surrounding the same may be filled with the saturated vapor of the liquid to be subjected to measurement, and a liquid drop is formed thereon using a microinjector. The size of the liquid drop is such that the contact diameter is about 3 mm or smaller. The contact angle can be determined by measuring the angle formed upon allowing the liquid drop to advance toward the solid surface (at the time when after the liquid is allowed to develop and spread on the specimen, the liquid drop becomes stable at a certain size) using a reading microscope (having a magnification of about 20) equipped with a goniometer. The visibility of the image becomes very good when the lens barrel is inclined by 1 to 2 degrees downward from the horizontal. The drop is illuminated from the front with light transmitted through an opalescent glass or with parallel beams of light transmitted through a heat ray-absorbing glass.

The contact angle data reported herein were measured by the method described later in the example section.

The high-molecular compound having an angle of contact with water within the range of 40° to 98° includes as typical examples, but is not limited to, synthetic high-molecular compounds such as nylon 6, nylon 6,6, nylon 11, polyethylene, poly(vinylidene chloride), poly(vinyl chloride), poly(vinyl acetate), polystyrene, styrene-divinylbenzene copolymers, poly(trifluoroethylene), poly(chlorotrifluoroethylene), polyethylene terephthalate), polypropylene, polyacrylic esters (e.g. poly(methyl acrylate)), polymethacrylic esters (e.g. poly(methyl methacrylate)), crosslinked polyacrylates and crosslinked polyamides as well as cellulose and like water-insoluble ones. Among them, polymers or copolymers produced by polymerizing an aromatic monomer or monomers (e.g. monomers selected from among alkylstyrenes which may optionally be substituted, for example methylstyrene and ethylstyrene; divinylbenzene and benzo-condensed cyclic compounds which may optionally be substituted, for example divinylnaphthalene and divinylanthracene) are preferred from the lymphocyte proliferation rate viewpoint. In particular, polystyrene and styrene-divinylbenzene copolymers are preferred.

Any conventional polystyrene species can be used as the polystyrene. The polystyrene is an arbitrary styrene polymer or styrene-based polymer.

The styrene-divinylbenzene copolymers can be obtained by crosslinking the above-mentioned styrene compound with m-, o- or p-divinylbenzene, which may optionally be substituted.

The high-molecular compound mentioned above may optionally be substituted by a halogen, alkyl, alkenyl, alkynyl, aralkyl, aryl, heteroaryl, arylcarbonyl, heteroarylcarbonyl, alkylcarbonyl, alkoxycarbonyl, arylsulfonyl, heteroarylsulfonyl, alkylsulfonyl, etc. The substituents mentioned above may further be substituted by a substituent(s) other than amines, and such substituents on the above-mentioned substituents are preferably other than amide, urea, ester and ether groups.

The high-molecular compound mentioned above is preferably one having no amine residue bound thereto. As the amine residue, there may be mentioned those residues resulting from chemical bonding of ammonia, primary to tertiary amine or the like to the high-molecular compound.

Further, the high-molecular compound mentioned above is preferably one comprising no other compound immobilized thereon. The other compound is not particularly restricted but includes, for example, amines, alcohols, glycidyl ethers, carboxylic acids and derivatives thereof, acid halides, halides, halogenated silanes, thiols, aldehydes and antibodies.

For the purpose of the present invention, namely from the lymphocyte proliferation promotion viewpoint, the above-mentioned angle of contact with water is preferably greater than 60° but not greater than 96°, more preferably about 70° to 94°, still more preferably about 75° to 91°.

In the practice of the invention, the porous material is preferably insoluble in water.

The porous material of the invention contains not less than about 50% by weight, preferably not less than about 60% by weight, more preferably not less than about 70% by weight, still more preferably not less than 80% by weight, of the high-molecular compound mentioned above.

As the component which can be contained in the porous material in addition to the above-mentioned high-molecular compound having an angle of contact with water within the range of 40° to 98°, there may be mentioned, for example, polyvinyl alcohol (contact angle 36°), poly(hydroxyethyl methacrylate) (contact angle 13°) and paraffin (contact angle 105 to 106°), among others.

By using two or more of the high-molecular compounds mentioned above having an angle of contact with water within the range of 40° to 98° in combination and/or by using any of the above-mentioned high-molecular compounds having an angle of contact with water of 40° to 98° as the main component and incorporating a component other than the high-molecular compound as the auxiliary material, among others, it is possible to adjust the angle of contact with water of the porous material to be obtained.

It is also preferred that the porous material have an angle of contact with water within the range of the angle of contact with water of the high-molecular compound mentioned above. Thus, the angle of contact with water of the porous material is preferably 40° to 98°, more preferably greater than 60° but not greater than 96°, still more preferably about 70° to 94°, particularly preferably about 75° to 91°.

The porous material of the invention occurs as a solid at ordinary temperature and ordinary pressure and has pores appropriate in size, namely has a porous structure.

As for the size of pores in the porous material, the molecular-weight exclusion limit of the water-insoluble porous material as determined using polystyrene beads is preferably not higher than $1.5 \times 10^5$, more preferably not higher than $1.4 \times 10^5$. When the molecular-weight exclusion limit is higher than $1.5 \times 10^5$, the level of unspecific adsorption tends to increase, the loss of useful proteins in the body fluid tends to occur and/or the ability of lymphocytes to proliferate tends to decrease with ease. For lessening the influence of unspecific adsorption while maintaining the lymphocyte proliferation rate at high levels, the molecular-weight exclusion limit is more preferably not higher than $1.3 \times 10^5$, particularly preferably not higher than $1.2 \times 10^5$, most preferably not higher than $1.0 \times 10^5$.

The molecular-weight exclusion limit can be easily controlled, for example, by adjusting the content of the above-mentioned high-molecular compound, which is the main constituent of the porous material, in the step of porous material production. Thus, as the content of the high-molecular compound increases, the molecular-weight exclusion limit lowers and, as the content of the high-molecular compound decreases, the molecular-weight exclusion limit rises.

The molecular-weight exclusion limit is the molecular weight of those molecules which cannot enter the pores (are excluded by the pores) in chromatography but are smallest in molecular weight among molecules incapable of enter the pores.

The molecular-weight exclusion limit can be measured in the following manner. Polystyrene beads differing in particle diameter are passed through a column packed with the porous material, and the pore size is determined on the basis of an excluded polystyrene beads-based exclusion curve. Then, the above-mentioned pore size is extrapolated to a spherical protein (e.g. dextran) the diameter and molecular weight of which are known, to thereby determine the molecular weight on the spherical protein equivalent basis; this is regarded as the molecular-weight exclusion limit.

The shape of the porous material may effectively be spherical, granular, flat membrane-like, fibrous, or hollow fiber-like, for instance. From the adsorption performance viewpoint, however, the spherical or granular form is more preferably used.

When the porous material is in a spherical or granular form, the average particle size thereof is preferably about 5 μm to 1,000 μm, more preferably about 20 to 800 μm, still more preferably about 30 to 600 μm.

The average particle diameter can be determined in the following manner. The porous material in a wet state is developed on a dish and scores of particles are photographed using a CCD camera. Then, the average particle diameter is calculated from the image captured using the particle diameter measurement software "Image-Pro plus" (product of Medical Cybernetics, Inc.).

The porous material of the invention can be produced, for example, in the following manner. One or more raw material monomer compounds are dispersed/suspended in a solvent having an appropriate viscosity (e.g. water). Suspension polymerization is carried out in the conventional manner while stirring the suspension to give the desired porous material.

Further, the porous material of the invention may also comprise activated carbon.

Usable as the activated carbon are, for example, fibrous activated carbon derived from phenolic fibers; coconut shell-derived activated carbon, petroleum pitch-derived activated carbon, peat-derived activated carbon, charcoal-based activated carbon and like granular activated carbon species.

The average particle diameter of the activated carbon is not particularly restricted but is preferably about 5 μm to 1,000 μm, more preferably about 20 to 800 μm, still more preferably about 30 to 600 μm.

Among the porous material components each comprising a high-molecular compound or activated carbon, polystyrene, styrene-divinylbenzene copolymers and activated carbon are preferred and, in particular, styrene-divinylbenzene copolymers are preferred, from the lymphocyte proliferation rate viewpoint.

As described hereinabove, activated carbon or a high-molecular compound having an angle of contact with water within the range of 40° to 98° can be used in producing the porous material for body fluid treatment for promoting the lymphocyte proliferation in lymphocyte culture.

Now, the treatment device of the invention is a treatment device for promoting lymphocyte proliferation in lymphocyte culture which comprises the porous material mentioned above as contained in a container.

The container to be used in the treatment device is not particularly restricted in shape, size or material.

The shape may be an arbitrary one, for example a sphere, container, bag, tube or column. As a preferred typical example, there may be mentioned, for example, a transparent or semitransparent cylindrical container with a capacity of about 0.1 to 400 ml and a diameter of about 0.1 to 10 cm.

The container can be manufactured using an arbitrary structure material. More specifically, as the structure material, mention may be made of unreactive polymers, biocompatible metals, alloys and glass, for instance.

As the unreactive polymers, there may be mentioned acrylonitrile-based polymers such as acrylonitrile-butadiene-styrene terpolymers; halogenated polymers such as polytetrafluoroethylene, polychlorotrifluoroethylene, tetrafluoroethylene-hexafluoropropylene copolymers and polyvinyl chloride; polyamides, polysulfones, polycarbonates, polyethylene, polypropylene, polyvinyl chloride-acrylic copolymers, polycarbonate-acrylonitrile-butadiene-styrene, polystyrene and polymethylpentene, among others.

As metallic materials useful as the container material, there may be mentioned stainless steel, titanium, platinum, tantalum, gold, and alloys thereof, as well as gold-plated alloy iron, platinum-plated alloy iron, cobalt-chromium alloys and titanium nitride-coated stainless steel, among others.

Materials resistant to autoclaving are particularly preferred and, specifically, silicone-coated glass, polypropylene, polyvinyl chloride, polycarbonates, polysulfones, polymethylpentene and the like may be mentioned as such materials.

The treatment device is preferably one comprising a container having a liquid inlet and a liquid outlet and equipped with means for preventing porous material leakage and the water-insoluble porous material packed in the container, though the device is not limited to such one.

The means for preventing porous material leakage may be a mesh, nonwoven fabric, cotton plug or like filter.

The method for proliferating lymphocytes according to the invention is now described.

The method for proliferating lymphocytes of the invention is a method which comprises bringing the above-mentioned porous material into contact with a body fluid and cultivating lymphocytes using the body fluid after contacting with the porous material.

As the method for proliferating lymphocytes of the invention, namely the treating method for promoting lymphocyte proliferation, there may specifically be mentioned such methods as mentioned below. (1) The method which comprises packing the treatment device (container having a body fluid inlet and a body fluid outlet and equipped, at the outlet, with a filter allowing the body fluid passage but allowing no porous material passage) with the porous material, bringing a body fluid into contact therewith and then using the same in lymphocyte cultivation, (2) the method which comprises collecting a body fluid in a bag already containing the porous material and, after a predetermined period of contacting, filtering off the porous material and using the filtrate in lymphocyte cultivation, and (3) the method which comprises causing the porous material to coexist in the lymphocyte culture system and filtering off the porous material from lymphocytes during cultivation or after completion of cultivation.

Referring to the method (1), the method for contacting consists, for example, in circulating the body fluid using a feed pump for a certain period of contacting or in allowing a certain period of contacting without circulation. As for the contacting time, 1 minute or a longer period of contacting is preferred and, from the adsorption performance viewpoint, about 15 minutes to 6 hours of contacting is more preferred. From the sufficient adsorption performance and cell treatment efficiency viewpoint, about 20 minutes to 4.5 hours of contacting is more preferred and about 30 minutes to 3 hours of contacting is still more preferred.

As the method (2), there are available, among others, the method which comprises collecting a body fluid directly in a bag already containing the porous material and effecting a certain period of contacting; and the method which comprises preparing a plasma or serum fraction from blood by centrifugation, for instance, placing the fraction in such a bag and effecting a certain period of contacting with the porous material. As for the contacting time, about 1 minute or a longer period of contacting is preferred and, from the adsorption performance viewpoint, about 10 minutes to 10 hours of contacting is more preferred and about 15 minutes to 6 hours of contacting is still more preferred. From the sufficient adsorption performance and cell treatment efficiency viewpoint, about 30 minutes to 3 hours of contacting is particularly preferred. As another method, it is also possible to add the porous material to a system wherein lymphocyte cultivation is in progress with patient's plasma added, for causing the porous material coexist in the system and, after the lapse of a certain period of time, the porous material is separated from lymphocytes by filtration using a filter allowing no passage of the porous material.

The temperature during contacting of the porous material with the body fluid in the above-mentioned method (1) or (2) can be arbitrarily selected but is preferably about 4° C. to 50° C., more preferably about 10° C. to 45° C.

Referring to the method (3), the porous material is caused to coexist with lymphocytes in a lymphocyte culture vessel and the porous material is separated from lymphocytes by filtration on the occasion of medium exchange or after completion of the cultivation. The contacting time is such that the contacting lasts until completion of lymphocyte cultivation at the longest, and the amount of the porous material to be added is preferably such that a sufficient space for lymphocyte proliferation can be secured without physical suppression thereof.

While the invention is not restricted to those mentioned above, the above method (1) is procedurally simple and most preferred as the method for overcoming lymphocyte proliferation inhibition in lymphocyte culture.

There may be some unknown mechanism of inhibiting the lymphocyte proliferation, as referred to hereinabove. An unknown "lymphocyte proliferation inhibiting factor" may be involved in that mechanism. Therefore, the porous material of the invention can function as an adsorbent for lymphocyte proliferation inhibiting factors.

When the treatment device mentioned above is used in carrying out the method for proliferating lymphocytes of the invention, an anticoagulant may be used.

As the anticoagulant, use may be made of any of heparin, low-molecular heparin, nafamostat mesilate, gebexate mesilate, argatroban, acid-citrate-dextrose (ACD) solution, citrate-phosphate-dextrose (CPD) solution and like citrate-containing anticoagulants, among others. Among them, heparin may generally be mentioned as the most preferred anticoagulant.

In the case of serum preparation, for instance, the above-mentioned anticoagulant may not be contained in the serum.

The body fluid so referred to herein includes blood, plasma and serum. In addition, the body fluid includes other body fluids, such as ascetic fluid, lymph and intraarticular fluid and fractions derived from these as well as other living body-derived fluid components.

For the purpose of the invention, it is a simple and easy way to collect blood from the subject and, if desired, prepare plasma by separation from blood corpuscle fractions by such means as centrifugation, for the subsequent use. Further, serum may be prepared for the subsequent use.

Also usable as the body fluid other than blood, plasma and serum are dilutions of these or supernatants obtained from them by pretreatment by specific gravity gradient centrifugation using Ficoll, Percoll, Vacutainer tube, Lymphoprep or the like.

While the body fluid may be used immediately after blood collection, refrigerated or lyophilized blood and preparations may also be used. Further, it is also possible to treat the body fluid using the adsorbent and then refrigerate or lyophilize the same, followed by thawing for use when required. The invention is not restricted to such modes, however.

The body fluid released from lymphocyte proliferation inhibition in lymphocyte culture, after lymphocyte proliferation promoting treatment according to the invention, can be obtained from the outlet side filter allowing no passage of the porous material as a result of filtering off of the porous material. When the target is blood, the desired plasma can be obtained by further carrying out a centrifugation procedure. It is also possible to obtain lymphocytes and the desired plasma simultaneously from the blood after treatment with the porous material by using Ficoll, Percoll, Vacutainer tube, Lymphoprep or the like.

The term "lymphocytes" as used herein refers to T cells and B cells, among others, occurring in mammalian peripheral blood, lymph vessels and bone marrow. The lymphocytes also include cells which are neither T cells nor B cells, for example natural killer cells. The T cells are not particularly restricted but include helper T cells, cytotoxic T cells and killer T cells.

In the practice of the invention, the lymphocyte culture can be carried out, for example, in the following manner. A mammalian body fluid is brought into contact with the porous material mentioned above and then sowed in a lymphocyte culture medium. The lymphocyte culture medium is incubated at an arbitrary temperature (preferably about 20° C. to 45° C., more preferably about 30° C. to 40° C., still more preferably about 37° C.) for an arbitrary period of time (for example about 3 days to 30 days, preferably about 7 days to 21 days, more preferably about 10 days to 18 days, most preferably about 14 days). As a result, lymphocytes proliferate.

The lymphocyte culture medium may be a conventional culture medium. Such medium includes, but is not limited to, such lymphocyte culture media as PB-MAX medium, AIM V medium, CHANG medium, LGM-3 medium, KBM400, GIT, Ham F-12, Dulbecco MEM, α-MEM, MEM, IMEM, RPMI-1640 and McCoy's 5A medium, among others.

On the occasion of lymphocyte culture, an antibody or the like can also be used to activate lymphocytes. As the antibody, there may be mentioned, for example, anti-CD3 antibody (OKT3) and so forth.

When the body fluid is a mammalian autologous body fluid and the mammal is in a condition of poor lymphocyte proliferation, the above-mentioned method for proliferating lymphocytes is more effective.

The term "poor lymphocyte proliferation" indicates that when patient's body fluid is added to a lymphocyte culture system, the lymphocyte proliferation rate is lower than the lymphocyte proliferation rate determined using a normal human-derived body fluid.

The lymphocyte proliferation rate is the proliferation rate (number of cells after 7 days/number of cells sowed) found after 1 week of lymphocytes cultivation at 37° C. using a culture medium supplemented with 0.1% (v/v) to 20% (v/v) of a patient-derived body fluid treated with the porous material or a normal human-derived body fluid not yet treated with the porous material.

In the case of packing a column with the porous material for using the same, it is important that clogging will never occur on the occasion of fluid passage, among others. For that reason, the porous material is required to have sufficient mechanical strength. Therefore, the porous material to be used in the practice of the invention is more preferably a hard one. In the case of a granular gel material, the term "hard one" as used herein refers to a gel which, when a cylindrical column is uniformly packed with the gel and an aqueous fluid is passed therethrough, shows a linear relationship between pressure loss $\Delta P$ and flow rate until about 0.3 kg/cm$^2$. In the case of using the porous material by placing the same in a bag, however, it may be a soft one.

Now, the method for producing mammalian lymphocytes according to the invention is a method which comprises bringing a mammalian body fluid into contact with the porous material mentioned above, cultivating lymphocytes using the body fluid after contacting with the porous material, and recovering lymphocytes produced.

The lymphocyte recovery can be carried out by any arbitrary method, for example by centrifugation, membrane filtration or chromatography.

Now, the method for manufacturing a pharmaceutical composition according to the invention is a method which comprises producing lymphocyte by the above-mentioned lymphocyte production method and blending the lymphocytes with a pharmaceutically acceptable additive.

As the pharmaceutically acceptable additive, there may be mentioned, for example, anticoagulants, vitamins and other nutrient sources, and antibiotics.

The pharmaceutical composition manufacture can be carried out using an acceptable pharmaceutical technique to give an appropriate galenic form composition (e.g. for transfusion, drip infusion or injection).

The additive body fluid of the invention, which is to be added to a culture medium on the occasion of lymphocyte culture, is one obtained by bringing a mammalian body fluid into contact with the porous material mentioned above.

The additive body fluid can be prepared, for example, by bringing a body fluid derived from a mammal with or without a disease against which a therapeutic effect is produced by extracorporeally activating lymphocytes and returning them into the body into contact with the porous material mentioned above.

Further, the method of the invention for treating a disease against which a therapeutic effect is produced by extracorporeally activating lymphocytes and returning them into the body is a method which comprises bringing a body fluid derived from a mammal requiring or not requiring treatment into contact with the porous material mentioned above, cultivating lymphocytes using the body fluid after contacting with the porous material, and administering the thus-obtained lymphocytes to the mammal.

The disease against which a therapeutic effect is produced by extracorporeally activating lymphocytes and returning them into the body includes, but is not limited to, cancer, infectious diseases and immune diseases, among others.

The activation includes, within the meaning thereof, an increase in the number of lymphocytes, a change in lymphocyte population as a result of proliferation and/or an improvement in the functions intrinsic in lymphocytes, and the like.

EFFECTS OF THE INVENTION

The present invention has made it possible to overcome the lymphocyte proliferation inhibition in lymphocyte culture and thus markedly increase the lymphocyte proliferation rate by adsorbing lymphocyte proliferation inhibiting factors from a body fluid derived from a subject with a disease against which a therapeutic effect is produced by extracorporeally activating lymphocytes and returning them into the body, for example a cancer subject with poor lymphocyte proliferation, without adsorbing factors necessary for lymphocyte proliferation from that body fluid. The invention is useful in that it provides a porous material for relieving the lymphocyte proliferation inhibition in lymphocyte culture using a target body fluid in activated autologous lymphocyte therapy, for instance, according to which a disease is treated or the progress of a disease is inhibited by taking immunocompetent cells (lymphocytes in particular) in blood out of the body, culturing them for stimulation/activation and for proliferation and again returning them into the body, as well as a method for proliferating lymphocytes which utilizes the above-mentioned porous material.

BEST MODES FOR CARRYING OUT THE INVENTION

The following examples specifically illustrate the present invention. These examples are, however, by no means limitative of the scope of the invention.

In the following examples etc., the angle of contact with water, molecular-weight exclusion limit and average particle diameter measurements were made in the following manner.

(1) Angle of Contact with Water

A flat and smooth film was prepared by compressing the high-molecular compound sample at a high pressure. The thus-obtained flat and smooth sheet specimen was placed horizontally, and a liquid drop was formed thereon using a microinjector. The size of the liquid drop was such that the contact diameter was about 1 to 2 mm. The contact angle was determined by measuring the angle formed upon allowing the liquid drop to advance toward the solid surface, at room temperature (20° C.), using a reading microscope (having a magnification of about 20) equipped with a goniometer.

(2) Molecular-Weight Exclusion Limit

Polystyrene beads differing in particle diameter were passed through a column packed with the porous material, and the pore size was determined on the basis of an excluded polystyrene beads-based exclusion curve. Then, the above-mentioned pore size was extrapolated to the spherical protein dextran the diameter and molecular weight of which were known, to thereby determine the molecular weight on the dextran equivalent basis; this was reported as the molecular-weight exclusion limit.

(3) Average Particle Diameter

The porous material in a wet state was developed on a dish and scores of particles were photographed using a CCD camera. Then, the average particle diameter was calculated from the image captured using the particle diameter measurement software "Image-Pro plus" (product of Medical Cybernetics, Inc.).

Example 1

(1) Lymphocyte Preparation

A winged needle for intravenous injection was connected to an adaptor and a holder was connected to the other end of the adaptor. The injection needle was stabbed into the brachial region of a normal subject and about 7.5 ml of blood was collected in a tube for lymphocyte separation (Vacutainer tube (product of Becton Dickinson and Company)). After blood collection, the Vacutainer tube was subjected to 20 minutes of centrifugation at 3,000 rpm at room temperature. The lymphocyte layer was recovered and supplemented with 40 ml of physiological saline, and the resulting mixture was centrifuged at 1,500 rpm at 4° C. for 5 minutes. This procedure was repeated several times for washing lymphocytes, and a lymphocyte suspension with a predetermined concentration was prepared by resuspending the lymphocytes in KBM 400 medium (product of Kohjin Bio Co., Ltd.).

(2) Preparation of a Plate with OKT3 Immobilized Thereon

OKT3 (product of Dainippon Pharmaceutical) was diluted to a concentration of 5 µg/ml with physiological saline, and the dilution was distributed in 500-µl portions into the wells of a 24-well polystyrene microplate (product of Sumitomo Bakelite Co., Ltd.). After 2 hours of standing still at room temperature, the OKT3 solution was removed, and the plate was washed with two equal portions of physiological saline; a plate with OKT3 immobilized thereon was thus prepared.

(3) Preparation of a Porous Material

A monomer mixture composed of 100 parts by weight of divinylbenzene for industrial use (divinylbenzene content 57%), 100 parts by weight of toluene, 60 parts by weight of isoamyl alcohol and 1 part by weight of benzoyl peroxide (content 75%) was added to an aqueous solution composed of 572 parts by weight of water, 23 parts by weight of sodium chloride, 1 part by weight of polyvinyl alcohol and 0.03 part by weight of sodium nitrite, and the polymerization was carried out at 80° C. in a nitrogen atmosphere for 5 hours with stirring so that droplets of the monomer mixture might be dispersed and suspended. The polymer particles formed were filtered off, washed with water and then deprived of such residual components as the solvent, monomer and initiator by extraction with acetone and again thoroughly washed with water and hot water. Porous styrene-divinylbenzene copolymer beads with a volume average particle diameter of about 400 µm were obtained (molecular-weight exclusion limit about $8 \times 10^4$, angle of contact with water about 85°).

(4) Plasma Treatment

The porous styrene-divinylbenzene copolymer beads were thoroughly washed with physiological saline and then 0.17 ml thereof were measured and placed in a cryotube. The physiological saline was thoroughly removed from the porous beads, 1 ml of cancer patient's serum was added thereto, followed by 2 hours of incubation at 37° C. with stirring (40 rpm) on a MIX rotor.

(5) Lymphocyte Cultivation

The plasma treated in the above manner was added to the lymphocyte culture medium KBM 400 (product of Kohjin Bio Co., Ltd.) to a concentration of 9% (v/v). Using the resulting culture medium, a lymphocyte suspension with a lymphocyte number of $1.0 \times 10^5$ cells/ml was prepared and sowed onto the previously prepared plate with OKT3 immobilized thereon in an amount of 444 µl/well (n=3 wells).

After 7 days of cultivation, lymphocytes were recovered and the number of cells was counted using a hemocytometer, and the lymphocyte proliferation rate was calculated according to the following formula (1).

Proliferation rate(times)=number of lymphocytes after 7 days of cultivation/number of lymphocytes sowed  (1)

As a result, in the case of treatment of cancer patient's plasma with the adsorbent, the number of lymphocytes increased to 16.7 times (proliferation rate) the number of cells sowed.

Example 2

The lymphocyte proliferation rate was determined in the same manner as in Example 1 except that petroleum pitch-derived activated carbon with a particle diameter of about 500 μm was used as the adsorbent in lieu of the porous styrene-divinylbenzene copolymer beads. As a result, the number of lymphocytes increased to 10.6 times (proliferation rate) the number of cells sowed.

Example 3

The lymphocyte proliferation rate was determined in the same manner as in Example 1 except that porous polystyrene (angle of contact with water about 85° C.) beads with a molecular weight exclusion limit of not higher than $1\times10^4$ and a particle diameter of about 400 μm were used. As a result, the number of lymphocytes increased to 11.5 times (proliferation rate) the number of cells sowed.

Example 4

Porous material preparation: A cellulose solution with a viscosity of about 1,000 cP was jetted, in the form of uniform droplets, into a gaseous phase under direct application of vibrations at a frequency of about 20,000 Hz to the solution. After causing the droplets to make a sufficient flight to take a spherical form, they were captured in a coagulation bath, deprived of the solvent and washed to give porous cellulose particles with a particle diameter of about 400 μm (molecular-weight exclusion limit not higher than $3\times10^4$, angle of contact with water about 50°).

The lymphocyte proliferation rate was determined in the same manner as in Example 1 except that the porous particles were used. As a result, the number of lymphocytes increased to 6.9 times (proliferation rate) the number of cells sowed.

Example 5

The lymphocyte proliferation rate was determined in the same manner as in Example 1 except that porous cellulose beads with a molecular-weight exclusion limit of not higher than $6\times10^4$ and a particle diameter of about 400 μm (angle of contact with water about 40°) were used. As a result, the number of lymphocytes increased to 5.7 times (proliferation rate) the number of cells sowed.

Comparative Example 1

The lymphocyte proliferation rate was determined in the same manner as in Example 1 except that the patient's plasma was used without contacting with any adsorbent. As a result, the number of lymphocytes increases to 3.9 times (proliferation rate) the number of cells sowed.

Comparative Example 2

The lymphocyte proliferation rate was determined in the same manner as in Example 1 except that the porous particles used in Example 4 were used after binding dextran sulfate thereto via epichlorohydrin (molecular-weight exclusion limit not higher than $3\times10^4$, angle of contact with water about 35°). As a result, the number of lymphocytes increased to 3.6 times (proliferation rate) the number of cells sowed.

Comparative Example 3

The lymphocyte proliferation rate was determined in the same manner as in Example 1 except that the porous particles used in Example 5 were used after binding dextran sulfate thereto via epichlorohydrin (molecular-weight exclusion limit not higher than $3\times10^4$, angle of contact with water about 30°). As a result, the number of lymphocytes increased to 3.2 times (proliferation rate) the number of cells sowed.

The results of the lymphocyte proliferation rate evaluation in Examples 1 to 5 and Comparative Examples 1 to 3 are shown in Table 1. From these results, it is evident that the lymphocyte proliferation rate could be markedly increased by cultivating lymphocytes using the specific porous materials of the invention after contacting with a body fluid as compared with the case of non-use of the porous material (adsorbent) or the cases where dextran sulfate was immobilized on the high-molecular compounds to render them hydrophilic.

TABLE 1

Influence of use of patient's plasma on lymphocyte proliferation
Lymphocyte proliferation rate after 7 days of cultivation
(calculated according to equation 1))

| | Lymphocyte proliferation rate (times) |
|---|---|
| Example 1 | 16.7 ± 3.2 |
| Example 2 | 10.6 ± 2.7 |
| Example 3 | 11.5 ± 3.0 |
| Example 4 | 6.9 ± 1.5 |
| Example 5 | 5.7 ± 1.6 |
| Comp. Ex. 1 | 3.9 ± 1.4 |
| Comp. Ex. 2 | 3.6 ± 0.8 |
| Comp. Ex. 3 | 3.2 ± 0.5 | n = 3 ± S.D

INDUSTRIAL APPLICABILITY

The present invention has made it possible to overcome the lymphocyte proliferation inhibition in lymphocyte culture and thus markedly increase the lymphocyte proliferation rate by adsorbing lymphocyte proliferation inhibiting factors from a body fluid derived from a subject with a disease against which a therapeutic effect is produced by extracorporeally activating lymphocytes and returning them into the body, for example a cancer subject with poor lymphocyte proliferation, without adsorbing factors necessary for lymphocyte proliferation from that body fluid. The invention is useful in that it provides a porous material for relieving the lymphocyte proliferation inhibition in lymphocyte culture using a target body fluid in activated autologous lymphocyte therapy, for instance, according to which a disease is treated or the progress of a disease is inhibited by taking immunocompetent cells (lymphocytes in particular) in blood out of the body, culturing them for stimulation/activation and for proliferation and again returning them into the body, as well as a method for proliferating lymphocytes which utilizes the above-mentioned porous material.

The invention claimed is:
1. A method for proliferating lymphocytes which comprises contacting a body fluid with a porous material which contains a polymer having an angle of contact with water within the range of 40° to 98° thereby removing lymphocyte proliferation inhibitor, wherein said polymer does not have a compound selected from the group consisting of amines, alcohols, glycidyl ethers, carboxylic acids and derivatives thereof, acid halides, halides, halogenated silanes, thiols, aldehydes and antibodies immobilized thereon, and adding together the lymphocytes in the body fluid after contacting with said porous material and a lymphocyte culture medium to culture lymphocytes.

2. The method according to claim 1, wherein the porous material has a molecular-weight exclusion limit of a polymer of not higher than $1.5 \times 10^5$ Dalton, wherein the molecular-weight exclusion limit is determined by passing polystyrene beads of differing particle diameter through a column packed with the porous material, determining the pore size on the basis of an excluded polystyrene beads-based exclusion curve; extrapolating the thus determined pore size to a spherical protein dextran of known diameter and molecular weight thereby determining the molecular weight on the dextran equivalent, which is the molecular-weight exclusion limit.

3. The method according to claim 1, wherein the polymer is an aromatic polymer.

4. The method according to claim 3, wherein the aromatic polymer is polystyrene or a styrene-divinylbenzene copolymer.

5. The method according to claim 1, wherein the polymer contains no amine residue bound thereto.

6. A method for proliferating lymphocytes which comprises contacting a body fluid with a porous material wherein the porous material further contains activated carbon thereby removing lymphocyte proliferation inhibitor.

7. The method according to claim 2, wherein the polymer is an aromatic polymer.

8. The method according to claim 2, wherein the polymer contains no amine residue bound thereto.

9. The method according to claim 3, wherein the polymer contains no amine residue bound thereto.

10. The method according to claim 4, wherein the polymer contains no amine residue bound thereto.

11. The method according to claim 1, which further comprises removing cells from the body fluid prior to the contacting of the body fluid with the porous material.

12. The method according to claim 1, wherein the body fluid is plasma.

* * * * *